United States Patent
Dogo-Isonagie et al.

(10) Patent No.: US 12,226,499 B2
(45) Date of Patent: *Feb. 18, 2025

(54) PEROXYMONOSULFATE ORAL WHITENING COMPOSITIONS

(71) Applicant: Colgate-Palmolive Company, New York, NY (US)

(72) Inventors: Cajetan Dogo-Isonagie, Mount Laurel, NJ (US); Suman Chopra, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/088,448

(22) Filed: Dec. 23, 2022

(65) Prior Publication Data

US 2023/0201091 A1  Jun. 29, 2023

Related U.S. Application Data

(60) Provisional application No. 63/293,345, filed on Dec. 23, 2021, provisional application No. 63/293,355, filed on Dec. 23, 2021.

(51) Int. Cl.
| | | |
|---|---|---|
| *A61K 8/23* | (2006.01) | |
| *A61K 8/24* | (2006.01) | |
| *A61K 8/44* | (2006.01) | |
| *A61K 8/46* | (2006.01) | |
| *A61K 8/81* | (2006.01) | |
| *A61K 8/86* | (2006.01) | |
| *A61K 8/90* | (2006.01) | |
| *A61Q 11/00* | (2006.01) | |
| *A61Q 11/02* | (2006.01) | |

(52) U.S. Cl.
CPC ............... *A61K 8/23* (2013.01); *A61K 8/24* (2013.01); *A61K 8/44* (2013.01); *A61K 8/463* (2013.01); *A61K 8/8111* (2013.01); *A61K 8/8176* (2013.01); *A61K 8/8182* (2013.01); *A61K 8/86* (2013.01); *A61K 8/90* (2013.01); *A61Q 11/00* (2013.01); *A61Q 11/02* (2013.01); *A61K 2800/43* (2013.01); *A61K 2800/48* (2013.01); *A61K 2800/52* (2013.01); *A61K 2800/522* (2013.01)

(58) Field of Classification Search
CPC .... A61Q 11/00; A61Q 11/02; A61K 2800/43; A61K 2800/48; A61K 2800/52; A61K 2800/522; A61K 8/23; A61K 8/24; A61K 8/44; A61K 8/463; A61K 8/8111; A61K 8/8176; A61K 8/8182; A61K 8/86; A61K 8/90

See application file for complete search history.

(56) References Cited

U.S. PATENT DOCUMENTS

| | | | |
|---|---|---|---|
| 10,299,998 | B2 | 5/2019 | Fei et al. |
| 10,709,646 | B2 | 7/2020 | Robbins et al. |
| 10,716,741 | B1 | 7/2020 | Yuan et al. |
| 10,716,742 | B2 | 7/2020 | Yuan et al. |
| 10,729,626 | B2 | 8/2020 | Potnis et al. |
| 10,744,075 | B2 | 8/2020 | Dogo-Isonagie et al. |
| 10,758,462 | B2 | 9/2020 | Yuan et al. |
| 10,973,885 | B2 | 4/2021 | Yuan et al. |
| 11,166,890 | B2 | 11/2021 | Dogo-Isonagie et al. |
| 11,229,588 | B2 | 1/2022 | Plata et al. |
| 2014/0377194 | A1* | 12/2014 | Strand ............ A61K 8/24 424/57 |
| 2017/0143599 | A1* | 5/2017 | Fei ................ A61K 8/463 |
| 2020/0138682 | A1 | 5/2020 | Galiyara et al. |
| 2020/0206123 | A1* | 7/2020 | Yuan ............. A61K 8/817 |

FOREIGN PATENT DOCUMENTS

| | | |
|---|---|---|
| WO | 2016/178652 | 11/2016 |
| WO | 2017/087442 | 5/2017 |
| WO | 2017/106067 | 6/2017 |
| WO | 2018/031018 | 2/2018 |
| WO | 2018/093356 | 5/2018 |
| WO | 2018/093357 | 5/2018 |

OTHER PUBLICATIONS

International Journal of Toxicology, vol. 27(Suppl 2), 2008, pp. 93-128 (Year: 2008).*
International Search Report and the Written Opinion of the International Searching Authority issued in International Application PCT/US2022/053991 mailed Apr. 20, 2023.
International Search Report and the Written Opinion of the International Searching Authority issued in International Application PCT/US2022/053992 mailed May 4, 2023.
Anais Pitto-Barry & Nicolas P. E. Barry, "Pluronic block-copolymers in medicine: from chemical and biological versatility to rationalization and clinical advances," Polymer Chemistry 2014, 5, 3291.
Andrew M. Bodratti & Paschalis Alexandridis, "Formulation of Poloxamers for Drug Delivery," Journal of Functional Biomaterials 2018, 9, 11.
Eleanora Russo & Carla Villa, "Poloxamer Hydrogels for Biomedical Applications," Pharmaceutics 2019, 11, 671.

\* cited by examiner

*Primary Examiner* — Walter E Webb
*Assistant Examiner* — Amanda Michelle Petritsch

(57) ABSTRACT

The present disclosure provides tooth whitening oral care compositions comprising potassium peroxymonosulfate having improved stability, and methods of using the same.

20 Claims, No Drawings

PEROXYMONOSULFATE ORAL WHITENING COMPOSITIONS

CROSS-REFERENCE TO RELATED APPLICATIONS

This application claims priority to, and the benefit of, U.S. Provisional Application No. 63/293,345, filed on Dec. 23, 2021, and U.S. Provisional Application No. 63/293,355, filed on Dec. 23, 2021, the contents of each of which are hereby incorporated by reference in their entireties.

BACKGROUND

Consumer products providing for teeth whitening are numerous and take many forms, but one of the more popular forms are as dentifrices, such as toothpastes. Toothpastes must typically have a semisolid form, able to hold shape well enough to be dispensed from a tube and rest on toothbrush bristles, but also fluid enough to be easily squeezed from the tube. Toothpastes must also be sticky enough to adhere to some degree to the teeth, but also soluble enough to disperse in the oral cavity. These different aims are commonly satisfied by formulating toothpastes in a high-water base (e.g., 10-40% water) with a mixture of liquid polar humectants, such as glycerin, polypropylene glycol, and sorbitol. Often various polymers are used to provide the gel-like consistency that is necessary for a toothpaste.

Unfortunately, many whitening agents have stability problems in the presence of water, humectants, and some polymers. Other inorganic species, such as fluoride sources and surfactants, can also interact negatively, resulting in instability and loss of activity of the active whitening agent. It thus becomes necessary to formulate a whitening toothpaste with various ingredients intended to improve stability and activity of the whitening agent active.

Abrasives can be particularly difficult to formulate into whitening toothpastes, because of the high surface area, hygroscopicity, and acidity of many abrasives. Yet abrasives can be a critical component of a whitening composition because many stains adhere strongly but superficially to the tooth surface and an abrasive helps remove such stains both by its intrinsic abrasive action and by providing better access of the whitening agent to the stain.

Products that are presently available to whiten teeth include a variety of different ingredients, and the primary active ingredient is most commonly a peroxide source such as hydrogen peroxide. The use of peroxide agents often presents numerous difficulties in both formulation and long-term stability of the resulting compositions. In addition, in high concentrations, or in prolonged contact with the oral mucosa, hydrogen peroxide can be highly irritating to the teeth and gums. Thus, alternative oxidizing agents with improved stability are needed, especially for whitening products which provide long-term contact with oral tissues.

Peroxysulfuric acid ($H_2SO_5$, also known as peroxymonosulfuric acid), and its salts, the peroxymonosulfates, are powerful oxidizing and stain removing agents. They are currently used for a variety of industrial and consumer purposes, including swimming pool treatment and denture cleaning. Peroxymonosulfate salts generally have the anion $[HSO_5]^-$, in contrast to the related peroxydisulfate salts which have the anion $[HS_2O_8]^-$. Peroxymonosulfate whitening products have been explored for some oral care applications, including whitening strips, mouthwashes and toothpastes. One common peroxymonosulfate oxidizing agent is potassium peroxymonosulfate ($KHSO_5$), also referred to as potassium monoperoxysulfate and abbreviated as KMPS or MPS, and sold as part of the compositions Oxone® and Caroat® (each of which is potassium peroxymonosulfate triple salt, having about 45-50 wt. % potassium peroxymonosulfate).

The use of potassium peroxymonosulfate in oral care applications has been very limited by its instability in aqueous solution, especially in aqueous solution near or above neutral pH. Potassium peroxymonosulfate has been known to degrade even in the presence of small quantities of water and heat. Thus, potassium peroxymonosulfate whitening compositions face particular difficulties in formulation.

Potassium peroxymonosulfate can also react and decompose when combined with other common oral care excipients, especially polar compounds, such as humectants, and anionic or neutral hydroxylic polymers and surfactants. These excipients can destabilize the potassium peroxymonosulfate, resulting in a loss of whitening efficacy. It therefore becomes necessary to adjust the formulations having potassium peroxymonosulfate to avoid or reduce the amount of such ingredients, which makes it challenging to still formulate a composition having desirable mouth feel (e.g., foaming), appearance, viscosity, and other important properties. Furthermore, potassium peroxymonosulfate can also interact negatively with any common flavoring agents, which tend to have labile or oxidizable functional groups. This can make it challenging to formulate flavors into such compositions.

There remains a need for tooth whitening dentifrice products based on peroxymonosulfate whitening agents with improved stability, mouthfeel, appearance, viscosity, flavor, and consumer acceptability.

BRIEF SUMMARY

The present disclosure provides a tooth whitening oral care composition comprising 0.01-10% potassium peroxymonosulfate by weight of the composition, stabilized with a combination of 21-60% calcium pyrophosphate ($Ca_2P_2O_7$) and/or insoluble sodium metaphosphate ($[NaPO_3]_n$) by weight of the composition, and 20-60% poloxamer (polyoxyethylene/polyoxypropylene triblock copolymer), by weight of the composition. In further embodiments, the compositions may further comprise one or more of polyvinylpyrrolidone, polyethylene glycol/polypropylene glycol random copolymer, polyethylene glycol, alkali metal polyphosphates, anionic surfactants, zwitterionic surfactants, cationic surfactants, and amphoteric surfactants. In at least one aspect, the tooth whitening oral care compositions of the present disclosure are low water or anhydrous.

Further areas of applicability of the present disclosure will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Open terms such as "include," "including," "contain," "containing" and the like mean "comprising." In this description, unless otherwise stated, the use of the singular also includes the plural. For example, "a lubricant" also comprehends the case where more than one lubricant is used.

"About" means plus or minus 20% of the stated value. Thus, for example, "about 5%" means from 80% to 120% of 5%, or 4.0% to 6.0%, inclusive of the end values of the range.

The inventors have unexpectedly found that the combination of 21-60% calcium pyrophosphate ($Ca_2P_2O_7$) and/or insoluble sodium metaphosphate ($[NaPO_3]_n$), and 20-60% polyoxyethylene/polyoxypropylene triblock copolymer, by weight of the composition, is highly effective in stabilizing potassium peroxymonosulfate against degradation, while also providing favorable rheological characteristics.

In a first aspect, the present disclosure provides a tooth whitening oral care composition (Composition 1) comprising 0.01-10% potassium peroxymonosulfate by weight, stabilized with a combination of 21-60% calcium pyrophosphate ($Ca_2P_2O_7$) and/or insoluble sodium metaphosphate ($[NaPO_3]_n$), by weight of the composition, and 20-60% polyoxyethylene/polyoxypropylene triblock copolymer, by weight of the composition. In further embodiments, the present disclosure provides:

1.1. Composition 1, wherein the potassium peroxymonosulfate is provided as a triple salt of potassium peroxymonosulfate, potassium hydrogen sulfate and potassium sulfate, optionally wherein the triple salt comprises about 45%-50% by weight of potassium peroxymonosulfate, e.g., 47% or 49% by weight of potassium peroxymonosulfate;

1.2. Composition 1 or 1.1, wherein the Composition comprises the potassium peroxymonosulfate in an amount of 0.01% to 5%, or 0.05% to 5%, or 0.1% to 5%, or 0.5% to 3%, or 0.5% to 2.5%, or 0.5% to 2%, or 0.5% to 1.5%, or 0.75% to 1.25%, or 1% to 5%, or 1% to 4%, or 1% to 3% or 1% to 2%, or 1.5% to 3%, or 2% to 3%, or 1.5% to 2%, or 2% to 2.5%, or about 0.5%, or about 1%, or about 1.5%, or about 2%, or about 2.5%, by weight of the composition;

1.3. Any of the preceding Compositions, wherein the inorganic peroxymonosulfate salt is not particulated (e.g., not granulated);

1.4. Any of the preceding Compositions, wherein the Composition does not comprise hydrogen peroxide;

1.5. Any of the preceding Compositions, wherein the Composition does not comprise any of hydrogen peroxide, urea peroxide, peroxide salts (e.g., sodium peroxide, potassium peroxide, lithium peroxide, calcium peroxide), peroxy acids (e.g., peroxyacetic acid, peroxybenzoic acid, or salts or derivatives thereof), organic peroxides (e.g., urea hydrogen peroxide, glyceryl hydrogen peroxide, peroxy esters, diacyl peroxides, monoperoxyphthalate, or salt thereof), perborate salts, persilicate salts, percarbonate salts, chlorinated oxidizing agents (e.g., hypochlorite salts, chlorite salts, chlorate salts, perchlorate salts, chlorine dioxide), or peroxydisulfuric acid or peroxydisulfate salts;

1.6. Any of the preceding Compositions, wherein the potassium peroxymonosulfate is the only oxidizing agent present in the Composition;

1.7. Composition 1, or any of 1.1-1.6, wherein the composition is stabilized by 21-60% calcium pyrophosphate ($Ca_2P_2O_7$) by weight of the composition;

1.8. Composition 1, or any of 1.1-1.6, wherein the composition is stabilized by 21-60% insoluble sodium metaphosphate ($[NaPO_3]_n$) by weight of the composition;

1.9. Composition 1, or any of 1.1-1.6, wherein the composition is stabilized by 21-60% calcium pyrophosphate ($Ca_2P_2O_7$) and insoluble sodium metaphosphate ($[NaPO_3]_n$) by weight of the composition;

1.10. Composition 1, or any of 1.1-1.9, wherein the Composition comprises the calcium pyrophosphate and/or the insoluble sodium metaphosphate in an amount of 22% to 60%, or 22% to 50%, or 22% to 40%, or 22% to 35%, or 25% to 60%, or 25% to 50%, or 25% to 40%, or 25% to 35%, or 25% to 30%, or 21% to 30%, or 22% to 30%, or 22.5% to 27.5%, or 23% to 27%, or 24% to 26%, or about 25%, by weight of the composition;

1.11. Composition 1, or any of 1.1-1.10, wherein the polyoxyethylene/polyoxypropylene triblock copolymer is a triblock copolymer having the formula $$HO-[CH_2CH_2O]_a[-CH(CH_3)CH_2O-]_b[CH_2CH_2O]_a-H,$$

wherein a is an integer between 1 and 30, b is an integer between 10 and 60;

1.12. Composition 1.11, wherein in said formula, a is an integer between 5 and 20, and b is an integer between 10 and 40;

1.13. Composition 1.11, wherein in said formula, a is an integer between 10 and 15, and b is an integer between 10 and 20;

1.14. Composition 1.11, wherein in said formula, a is an integer between 10 and 12 (e.g., 11), and b is an integer between 15 and 20 (e.g., 16);

1.15. Composition 1, or any of 1.1-1.14, wherein the polyoxyethylene/polyoxypropylene triblock copolymer has an average molecular weight of 1000 to 7000 Daltons, e.g., 1000 to 6000 Daltons, or 1000 to 5000 Daltons, or 1000 to 4000 Daltons, or 1000 to 3000 Daltons, or 1000 to 2000 Daltons, or 1500 to 3000 Daltons, or 1500 to 2000 Daltons, or 1800 to 2000 Daltons, or about 1900 Daltons, optionally wherein said average molecular weight is a number average molecular weight or a weight average molecular weight;

1.16. Composition 1.11, wherein the polyoxyethylene/polyoxypropylene triblock copolymer is Pluronic L35;

1.17. Composition 1, or any of 1.1-1.16, wherein the Composition comprises the polyoxyethylene/polyoxypropylene triblock copolymer in an amount of 22% to 60%, or 22% to 50%, or 22% to 40%, or 22% to 35%, or 25% to 60%, or 25% to 50%, or 25% to 40%, or 25% to 35%, or 27% to 33%, or 28% to 32%, or 30% to 32%, or about 30%, or about 31%, by weight of the composition;

1.18. Any preceding Composition, wherein the Composition further comprises one or more of polyvinylpyrrolidone, polyethylene glycol/polypropylene glycol random copolymer, polyethylene glycol, polyphosphates (e.g., alkali metal polyphosphates), and surfactants (e.g., anionic and/or zwitterionic surfactants);

1.19. Composition 1.18, wherein the Composition further comprises polyvinylpyrrolidone;

1.20. Composition 1.19, wherein the polyvinylpyrrolidone is cross-linked polyvinylpyrrolidone;

1.21. Composition 1.19 or 1.20, wherein the polyvinylpyrrolidone is not complexed with or combined with hydrogen peroxide;

1.22. Any of Compositions 1.19-1.21, wherein the Composition comprises the polyvinylpyrrolidone in an amount of 1% to 50%, or 1% to 40%, or 1% to 30%, or 1% to 25%, or 1% to 22%, or 1% to 20%, or 1% to 18%, or 1% to 15%, or 1% to 12%, or 1% to 10%, or 1% to 8%, or 1% to 6%, or 3% to 15%, or 3% to 12%, or 3% to 10%, or 3% to 8%, or 3% to 6%, or 4% to 8%, or 4% to 6%, or about 5%, by weight of the composition;

1.23. Any of Compositions 1.18-1.22, wherein the Composition further comprises a polyethylene glycol/polypropylene glycol random copolymer (PEG/PPG copolymer);

1.24. Composition 1.23, wherein the PEG/PPG random copolymer has an average molar ratio of ethylene glycol units (EG) to propylene glycol units (PG) of about 75-150 EG to 45-95 PG, or about 95-135 EG to 50 to 80 PG, or about 105-125 EG to 55-75 PG, or about 110-120 EG to 60-70 PG, or about 116 EG to 66 PG (i.e., PEG/PPG 116/66);

1.25. Composition 1.23 wherein the PEG/PPG random copolymer is Pluracare L1220;

1.26. Any of Compositions 1.23-1.25, wherein the Composition comprises the PEG/PPG random copolymer in an amount of 1% to 50%, or 1% to 40%, or 1% to 30%, or 1% to 25%, or 1% to 20%, or 1% to 18%, or 1% to 15%, or 1% to 12%, or 1% to 10%, or 6% to 40%, or 6% to 30%, or 6% to 25%, or 6% to 20%, or 6% to 15%, or 6% to 10%, or 8% to 30%, or 8% to 25%, or 8% to 20%, or 8% to 15%, or 8% to 12%, or 10% to 30%, or 10% to 25%, or 10% to 20%, or 10% to 15%, or 10% to 12%, or about 10%, by weight of the composition;

1.27. Any of Compositions 1.18-1.26, wherein the Composition further comprises polyethylene glycol;

1.28. Composition 1.27, wherein the polyethylene glycol is selected from the group consisting of PEG-200, PEG-300, PEG-400, PEG-500, PEG-600, PEG-800, PEG-1000, PEG-1600, and PEG-2000;

1.29. Composition 1.27, wherein the polyethylene glycol is PEG 600;

1.30. Any of Compositions 1.27-1.29, wherein the Composition comprises the polyethylene glycol in an amount of 1 to 50%, or 1 to 40%, or 1 to 30%, or 1 to 25%, or 1 to 20%, or 1 to 18%, or 1 to 15%, or 5 to 40%, or 5 to 30%, or 5 to 25%, or 5 to 20%, or 5 to 15%, or 8 to 40%, or 8 to 30%, or 8 to 25%, or 8 to 20%, or 8 to 15%, or 10 to 30%, or 10 to 25%, or 10 to 20%, or 10 to 15%, or 12 to 25%, or 12 to 20%, or 12 to 15%, or about 12% (e.g., about 12.5%), by weight of the composition;

1.31. Any preceding composition, wherein the Composition further comprise one or more additional polymers, such as, any one or more of: polypropylene glycols, polysaccharides (e.g., cellulose derivatives, for example carboxymethyl cellulose, hydroxypropyl cellulose, hydroxypropyl methyl cellulose, ethyl cellulose, microcrystalline cellulose; or polysaccharide gums, for example xanthan gum, guar gum, or carrageenan gum, pectins, karaya gum); chitosans; dextrans; hyaluronic acid and sodium hyaluronates; synthetic anionic polymeric polycarboxylates, such as copolymers of maleic anhydride or acid with another polymerizable ethylenically unsaturated monomer, preferably methyl vinyl ether (e.g., copolymers in a 1:4 to 4:1 ratio of maleic anhydride/acid to methyl vinyl ether); polyphosphonic acids and polyphosphonates (i.e., polyphosphoesters); cross-linked carboxyvinyl copolymers; polyacrylic acid or polyacrylate polymers (e.g. carbomers); polyacrylamides, such as (2-hydroxypropyl)methacrylamide; other polyoxyethylene-polyoxypropylene copolymers (PEG-PPG) tri-block copolymers, such as poloxamer 105, 108, 122, 123, 124, 182, 183, 184, 185, 188, 212, 215, 217, 234, 235, 237, 238, 288, 333, 334, 335, 338, 402, 403, or 407); PEG-PPG tetrablock copolymers; other PEG/PPG random copolymers, such as PEG/PPG-38/8; polyamines; polyvinyl alcohols; polyoxazolines, such as poly(2-alkyl-2-oxazolines), e.g., methyl, ethyl, or isopropyl substituted polyoxazolines; and quaternary ammonium polymers;

1.32. Composition 1, or any of Compositions 1.1-1.31, wherein the Composition does not comprise any one or more of: polyacrylic acid or polyacrylate polymers (PAA), polyvinylpyrrolidone-vinyl acetate copolymers (PVP-VA), polyoxazoline polymers (PO), and mixtures thereof;

1.33. Composition 1, or any of Compositions 1.1-1.31, wherein the Composition comprises 30 to 70% by weight of polymers (e.g., PEG/PPG random copolymer, PEG/PPG triblock copolymer, PVP, and PEG), e.g., 30 to 60% by weight, or 40 to 60% by weight, or 50 to 60% by weight, or 55 to 60% by weight, or 55 to 59% by weight, or 58 to 59% by weight;

1.34. Any preceding Composition, wherein the Composition further comprises a polyphosphate or an organic cyclic polyphosphate, such as an alkali metal pyrophosphate, an alkali metal tripolyphosphate, an alkali metal tetraphosphate, an alkali metal hexametaphosphate, an alkali metal insoluble metaphosphate, an alkali metal phytic acid salt, or a mixture thereof;

1.35. Composition 1.34, wherein the Composition comprises a sodium or potassium pyrophosphate, a sodium or potassium tripolyphosphate, a sodium or potassium tetraphosphate, a sodium or potassium phytic acid salt, or a mixture thereof;

1.36. Composition 1.34, wherein the Composition comprises a tetra-alkali metal pyrophosphate, e.g., tetrasodium or tetrapotassium pyrophosphate;

1.37. Composition 1.34, wherein the Composition comprises a di-alkali metal pyrophosphate, e.g., disodium pyrophosphate or dipotassium pyrophosphate;

1.38. Composition 1.34, wherein the Composition comprises a tetra-alkali metal pyrophosphate and a di-alkali metal pyrophosphate, e.g., tetrasodium pyrophosphate and disodium pyrophosphate;

1.39. Any of Compositions 1.34-1.38, wherein the Composition comprises from 0.1 to 5% by weight of polyphosphates, e.g., 0.5 to 5%, or 1% to 5%, or 2% to 5%, or 3 to 5%, or 3.5% to 5%, or 4% to 5%, or 3.5% to 4.5%, or about 4% by weight of polyphosphates, optionally 1-5% or 2-4% of a tetra-alkali metal pyrophosphate and 0.5-2% of a di-alkali metal pyrophosphate, e.g., about 3% tetrasodium pyrophosphate and about 1% disodium pyrophosphate;

1.40. Any preceding Composition, wherein the Composition further comprises one or more surfactants, e.g., anionic surfactants, cationic surfactants, amphoteric, non-ionic, and/or zwitterionic surfactants;

1.41. Composition 1.40, wherein the Composition comprises a mixture of anionic and zwitterionic surfactants;

1.42. Composition 1.40 or 1.41, wherein said anionic surfactants are selected from: sodium lauryl sulfate, sodium laureth sulfate, sodium myreth sulfate, sodium lauroyl sarcosinate, sodium coconut monoglyceride sulfonates, sodium lauryl benzene sulfonate, sodium lauryl sulfoacetate, sodium N-methyl N-cocoyl taurate, sodium cocoyl isethionate, sodium dioctyl sulfosuccinate, and sodium cocomonoglyceride sulfate, and ammonium analogs thereof;

1.43. Composition 1.40 or 1.41, wherein said zwitterionic surfactants are selected from: cocamidopropyl betaine (CAPB), cocamidopropyl sultaine, cocamidopropyl hydroxysultaine, lauramidopropyl betaine, lauramidopropyl sultaine, lauramidopropyl hydroxysultaine, oleamidopropyl betaine, oleamidopropyl sultaine, oleamidopropyl hydroxysultaine, tallowamideopropyl betaine, tallowamidopropyl sultaine, tallowamidopropyl hydroxysultaine, lauryl betaine, lauryl sultaine, lauryl hydroxysultaine, lauryldimethylamine oxide, and myristamine oxide;

1.44. Composition 1.40, wherein said cationic surfactants are selected from: cetylpyridinium chloride (CPC), cetrimonium bromide, benzalkonium chloride, benzethonium chloride (1-hexadecylcarbamoyl-ethyl)-trimethylammonium halide, (1-hexadecylcarbamoyl-2-phenyl-ethyl)-trimethylammonium halide, 1-hexadecylcarbamoyl-1,1-dimethyl-pyrrolidinium halide, and [2-(1H-indole-3-yl)-1-hexadecylcarbamoyl-ethyl)]-trimethylammonium halide, wherein said halide is optionally chloride, fluoride or bromide, or lauroyl arginine, ethyl lauroyl arginine ester hydrochloride, or disodium sebacoyl bis-lauramidolysine;

1.45. Composition 1.40, wherein said non-ionic surfactants are selected from: cocomnoethanolamide, cocodiethanolanide, laurylamidopropyl dimnethylamine oxide, myristylamnidopropyl dimethylamine oxide, and decyl glucoside;

1.46. Any of Compositions 1.40 to 1.45, wherein the Composition comprises sodium lauryl sulfate;

1.47. Any of Composition 1.40 to 1.45, wherein the Composition comprises cocamidopropyl betaine;

1.48. Composition 1.39 or 1.40, wherein the Composition comprises a mixture of sodium lauryl sulfate and cocamidopropyl betaine;

1.49. Any of Compositions 1.40-1.48, wherein the Composition comprises 0.1 to 5% of surfactants, e.g., 0.5% to 5%, or 1 to 5%, or 1.5 to 5%, or 2 to 5%, or 3 to 5%, or 4 to 5%, or 1 to 4%, or 2 to 4%, or 3 to 4%, or 2 to 5%, or 3 to 5%, or 1 to 3%, or 2 to 3%, or 2 to 2.5%, or 2.5 to 3%, or 2.25 to 2.75%, or 2.25 to 2.5%, or about 2.3%, by weight of the composition;

1.50. Any of Compositions 1.40-1.49, wherein the Composition comprises any one or more surfactants in an individual amount of 0.1 to 5%, e.g., 0.1% to 4%, or 0.1 to 3%, or 0.1 to 2.5%, or 0.1 to 2%, or 0.1 to 1.5%, or 0.1 to 1%, or 0.1 to 0.5%, or 1 to 4%, or 2 to 4%, or 1 to 3%, or 2 to 3%, or 1.5 to 2.5%, or 2 to 2.5%, or about 0.3% or about 2%, by weight of the composition;

1.51. Any of Compositions 1.40-1.50, wherein the Composition comprises 0.1 to 5%, or 1 to 5%, or 2 to 4%, or 1 to 3%, or 2 to 3%, or 1.5 to 2.5%, or 2 to 2.5%, or about 2%, of sodium lauryl sulfate, and 0.1 to 1%, or 0.1 to 0.5%, or about 0.3%, of cocamidopropylbetaine, by weight of the composition;

1.52. Any of Compositions 1.40-1.51, wherein the Composition comprises an anionic surfactant (e.g., sodium lauryl sulfate) and a zwitterionic surfactant (e.g., cocamidpropylbetaine) in a weight ratio of about 20:1 to 1:1, e.g., about 20:1 to 2:1, or about 15:1 to 3:1, or about 12:1 to 4:1, or about 10:1 to 5:1, or about 8:1 to 5:1, or about 7:1 to 5:1, or about 6:1;

1.53. Any preceding Composition, wherein the Composition further comprises an antioxidant, e.g., selected from butylated hydroxyanisole, butylated hydroxytoluene, vitamin A, carotenoids, vitamin E, flavonoids, polyphenols, ascorbic acid, and mixtures thereof;

1.54. Composition 1.53, wherein the antioxidant is butylated hydroxyanisole or butylated hydroxytoluene;

1.55. Composition 1.53, wherein the antioxidant is butylated hydroxytoluene;

1.56. Any of Compositions 1.52-1.55, wherein the Composition comprises any one or more antioxidants in an individual amount of 0.001 to 1%, e.g., 0.01% to 0.5%, or 0.01 to 0.3%, or 0.01 to 0.1%, or 0.01 to 0.05%, or about 0.03%, by weight of the composition;

1.57. Any preceding Composition, wherein the Composition further comprises a thickening agent, e.g., magnesium aluminum silicate, or fumed silica, optionally in an amount of 0.1 to 10% by weight of the composition, e.g., 1 to 10%, or 2.5 to 10%, or 3 to 10%, or 2.5 to 7.5%, or 3 to 8%, or 3 to 6%, or 3 to 5%, or about 4%, by weight of the composition;

1.58. Any preceding Composition, wherein the Composition further comprises a fluoride source;

1.59. Composition 1.58, wherein the fluoride source is selected from sodium fluoride, sodium monofluorophosphate, and stannous fluoride, or mixtures thereof;

1.60. Composition 1.58 or 1.59, wherein the Composition comprises 0.1 to 5% of fluoride source(s) by weight of the composition, e.g., 0.5 to 5%, or 0.5 to 3%, or 0.5 to 2%, or 0.5 to 1%, or about 0.75%, by weight of the composition;

1.61. Any preceding Composition, wherein the Composition further comprises an additional abrasive (i.e., in addition to the calcium pyrophosphate and/or the insoluble sodium metaphosphate), optionally wherein the Composition does not comprise a hydrated silica or precipitated silica abrasive (e.g., synthetic high-cleaning silica);

1.62. Composition 1.61, wherein the additional abrasive is selected from silica (e.g., hydrated silica, precipitated silica), calcium carbonate, calcium orthophosphate, dicalcium orthophosphate, tricalcium phosphate, and arginine carbonate, e.g., in an amount of 0.1 to 10%, or 0.1 to 5%, or 1 to 5%, or 2.5 to 5%;

1.63. Any preceding Composition, wherein the Composition further comprises a desensitizing agent, e.g., in an amount from 0.1 to 5% by weight, such as potassium nitrate;

1.64. Any preceding Composition, wherein the Composition further comprises an enamel strengthening agent, e.g., in an amount from 0.1 to 5% by weight, such as zinc phosphate;

1.65. Any preceding Composition, wherein the Composition further comprises one or more of flavors and sweeteners, e.g., in an amount of 0.1 to 5%, or 0.5 to 5%, or 1 to 5%, or 2 to 5%, or 2 to 3%;

1.66. Any preceding Composition, wherein the Composition is substantially anhydrous (e.g., less than 4%, or less than 3%, or less than 2%, or less than 1% water by weight of the composition);

1.67. Any preceding Composition, wherein the Composition does not comprise any acetate esters, for example, wherein the Composition does not comprise any of: triacetin, glyceryl acetate, propylene glycol diacetate, ethylene glycol diacetate, and diethylene glycol diacetate;

1.68. Any preceding Composition, wherein the Composition does not comprise any humectants, for example, wherein the Composition does not comprise any of glycerol, propylene glycol, sorbitol, or xylitol;

1.69. Composition 1, or any of 1.1-1.68, wherein the composition comprises 1 to 3% of sodium lauryl sulfate, and 0.1 to 0.5% of cocamidopropyl betaine, by weight of the composition;

1.70. Composition 1, or any of 1.1-1.68, wherein the composition comprises 1.5 to 2.5% of sodium lauryl sulfate, and 0.2 to 0.4% of cocamidopropyl betaine, by weight of the composition;

1.71. Composition 1, or any of 1.1-1.68, wherein the composition comprises about 2% of sodium lauryl sulfate, and about 0.3% of cocamidopropyl betaine, by weight of the composition;

1.72. Composition 1, or any of Compositions 1.1-1.71, wherein the Composition comprises sodium lauryl sulfate and cocamidopropyl betaine in a weight ratio of about 8:1 to 5:1, e.g., about 6:1;

1.73. Any preceding Composition, wherein the Composition comprises the potassium peroxymonosulfate in an amount of 1% to 5%, and the composition is stabilized by a combination of 20-40% calcium pyrophosphate and 25-50% of a polyoxyethylene/polyoxypropylene triblock copolymer having the formula

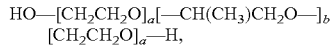
HO—[CH$_2$CH$_2$O]$_a$[—CH(CH$_3$)CH$_2$O—]$_b$
[CH$_2$CH$_2$O]$_a$—H, wherein an integer between 10 and 12 (e.g., 11), and b is an integer between 15 and 20 (e.g., 16), e.g., the polymer is Pluronic L35, each by weight of the composition;

1.74. Any preceding Composition, wherein the Composition comprises the potassium peroxymonosulfate in an amount of 1% to 3%, and the composition is stabilized by a combination of 20-30% calcium pyrophosphate and 25-35% of a polyoxyethylene/polyoxypropylene triblock copolymer having the formula

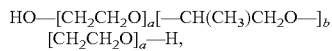
HO—[CH$_2$CH$_2$O]$_a$[—CH(CH$_3$)CH$_2$O—]$_b$
[CH$_2$CH$_2$O]$_a$—H, wherein an integer between 10 and 12 (e.g., 11), and b is an integer between 15 and 20 (e.g., 16), e.g., the polymer is Pluronic L35, each by weight of the composition;

1.75. Any preceding Composition, wherein the Composition further comprises polyvinylpyrrolidone in an amount of 1 to 10%, and PEG/PPG random copolymer having an average molar ratio of ethylene glycol units (EG) to propylene glycol units (PG) of about 105-125 EG to 55-75 PG (e.g., Pluracare L1220 polymer) in an amount of 6 to 15%, and polyethylene glycol 600 in an amount of 5 to 20%, each by weight of the composition;

1.76. Any preceding Composition, wherein the Composition further comprises 2% to 5% tetrasodium pyrophosphate and 0.5 to 1.5% disodium pyrophosphate, by weight of the composition;

1.77. Any preceding Composition, wherein the Composition further comprises a blue dye or pigment, e.g., Blue 15 pigment (also known as CI 74160), optionally in an amount of 0.001 to 0.1% by weight of the composition, e.g., 0.01 to 0.08%, or 0.03 to 0.07%, or about 0.05%, by weight of the composition;

1.78. Composition 1 or any of 1.1-1.77, wherein the Composition comprises or consists of:

| Ingredient | Weight % |
|---|---|
| Potassium peroxymonosulfate | 0.1-5% (e.g., about 1%) |
| Calcium pyrophosphate | 21-30% (e.g., about 25%) |
| PEG/PPG triblock copolymer (e.g., Pluronic L35) | 25-35% (e.g., 30-32% or about 31%) |
| Polyvinylpyrrolidone | 1-15% (e.g., about 5%) |
| PEG-PPG random copolymer (e.g., PEG/PPG-116/66) | 6-15% (e.g., about 10%) |
| Polyethylene glycol (e.g., PEG 600) | 10-20% (e.g., about 12.5%) |
| Polyphosphate (e.g., tetrasodium and disodium pyrophosphates) | 2.5-5% (e.g., about 4%) |
| Anionic Surfactant (e.g., sodium lauryl sulfate) | 1-5% (e.g., about 2%) |
| Zwitterionic Surfactant (e.g., cocamidopropyl betaine) | 0.1-1% (e.g., about 0.3%) |
| Fluoride source (e.g., sodium monofluorophosphate) | 0.1 to 2% (e.g., about 0.76% or 1.1%) |
| Antioxidant (e.g., BHT) | 0 to 0.3% (e.g., 0 or about 0.03%) |
| Thickener (e.g., fumed silica) | 2.5-5% (e.g., about 4%) |
| Sweeteners and Flavors | 0.5-5% (e.g., 3-3.5%) |
| Blue pigment or dye (e.g., Blue 15) | 0.001 to 0.1% (e.g., about 0.05%) |
| Total | ca. 100 |

1.79. Any preceding Composition, wherein the composition is a dentifrice, e.g., a toothpaste or a tooth gel;

1.80. Any preceding Composition, wherein the composition has the consistency of a paste or gel (e.g., not a free-flowing liquid and not a solid, such as a solid powder or pellets);

1.81. Any preceding Composition, wherein the Composition has a squeeze pressure of 0.03 to 0.2 bar, e.g., 0.03 to 0.15 bar, or 0.03 to 0.10 bar, or 0.03 to 0.07 bar, or 0.04 to 0.06 bar, or about 0.05 bar;

1.82. Any preceding Composition, wherein the Composition has a viscosity (measured at 1 rpm) of 50,000 to 300,000 cP, e.g., 100,000 to 300,000 cP, or 150,000 to 250,000 cP, or 175,000 to 225,000 cP, or about 200,000 cP;

1.83. Any preceding Composition, wherein after up to 3 months of aging at 40° C./65% relative humidity, the Composition retains a squeeze pressure below 0.1 bar and/or a viscosity (at 1 rpm) below 300,000 cP;

1.84. Any preceding Composition, wherein the composition loses not more than 10% of its initial active oxygen (AO) content after up to 3 months of aging at 60° C./75% relative humidity.

Potassium peroxymonosulfate (also known as MPS, KMPS, potassium monopersulfate, or potassium monoperoxysulfate) is commercially available as Caroat® or Oxone®, both of which are a triple salt of potassium peroxymonosulfate, potassium hydrogen sulfate and potassium sulfate (2KHSO$_5$·KHSO$_4$·K$_2$SO$_4$).

Potassium peroxymonosulfate has limited stability in aqueous solutions and can be destabilized by other common toothpaste ingredients, even small amounts of water. Therefore, contact with water during processing and storage should be avoided or minimized. The compositions are preferably packaged in a moisture free environment.

As used herein, the term "insoluble sodium metaphosphate" is used to refer to the insoluble polymeric sodium metaphosphate, which has the empirical formula $[NaPO_3]_n$, also known as "Maddrell's Salt." This is a highly useful abrasive, which is insoluble in water and has a low capacity for releasing phosphate ion into solution. It has a high molecular weight, with values of n up to 2000. It is distinct from such soluble species as trisodium orthophosphate ($Na_3PO_4$), tetrasodium pyrophosphate ($Na_4P_2O_7$), pentasodium tripolyphosphate ($Na_5P_3O_{10}$), hexasodium tetraphosphate ($Na_6P_4O_{13}$), sodium trimetaphosphate ($Na_3[(PO_3)_3)]$), or sodium hexametaphosphate ($Na_6[(PO_3)_6)]$), all of which are water soluble and prone to hydrolysis under aqueous conditions to provide orthophosphate anion.

The compositions of the present disclosure contain no water or have a low water content. As used herein, the term "low water content" means the total concentration of water, including any free water and all water contained in any ingredients. In various embodiments of the composition, the amount of water is in an amount of less than 4% by weight, or less than 3% by weight, or less than 2% by weight, or less than 1% by weight, or less than 0.5% by weight, or less than 0.1%, or about 0.0001% to about 4% by weight, or about 0.0001% to about 0.5% by weight or about 0.0001% to about 0.1% by weight.

The amount of potassium peroxymonosulfate in the compositions of the invention is effective to result in improved tooth whitening when used once or twice daily for about three months as compared to a control composition without the peroxymonosulfate salt. The amount of peroxymonosulfate salt typically is about 0.1% to about 10%, by weight of the composition, preferably about 1 wt. % or 2 wt. %.

In some embodiments, the compositions of the present disclosure contain a buffering agent. Examples of buffering agents include anhydrous carbonates such as sodium carbonate, sesquicarbonates, bicarbonates such as sodium bicarbonate, silicates, bisulfates, phosphates such as monopotassium phosphate and dipotassium phosphate, citrates, pyrophosphates (sodium and potassium salts) and combinations thereof. The amount of buffering agent is sufficient to provide a pH of about 5 to about 9, preferable about 6 to about 8, and more preferable about 7, when the strip is hydrated. Typical amounts of buffering agent are about 0.1% to about 5%, in one embodiment about 1% to about 3%, in another embodiment about 0.5% to about 1%, by weight of the total composition.

The compositions of the present disclosure comprise a polyoxyethylene-polyoxypropylene triblock copolymer, also known as a poloxamer. The term "poloxamer" or "poloxamer copolymer" refers to a nonionic triblock copolymer composed of a central hydrophobic chain of polyoxypropylene units (a.k.a. poly(propylene oxide) units) flanked by two hydrophilic chains of polyoxyethylene units (e.g., poly(ethylene oxide) units). Poloxamers have the following chemical structure:

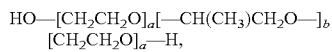

wherein a and b are integers, each typically between 10 and 200. Poloxamers are named according to common conventions based on their molecular weight and ethoxy content, and include poloxamer 407, poloxamer 338, poloxamer 237, poloxamer 188 and poloxamer 124. Pluronic is the name of a line of poloxamer polymers manufactured by BASF. For example, Pluronic F-127 is poloxamer 407. Poloxamers are distinguished from other polyethylene glycol/polypropylene glycol copolymers (PEG/PPG copolymers or EO/PO copolymers) which have a structure other than as a triblock structure, such as a random copolymer structure, Such copolymers that are distinct from poloxamers include the PEG/PPG copolymers sold by BASF as the Pluracare® and Pluraflo® series polymers, which are random PEG/PPG copolymers.

For example, suitable poloxamers may include one or more of Pluronic® L35, Pluronic® L43, Pluronic® L64, Pluronic® L 10, Pluronic® L44, Pluronic® L62, Pluronic® 10RS, Pluronic® 17R4, Pluronic® L25R4, Pluronic® P84, Pluronic® P65, Pluronic® PI 04, and Pluronic® PI 05. Pluronic® brand dispersants are commercially available from BASF, Florham Park, N.

In some embodiments, the compositions of the present disclosure may comprise polyvinylpyrrolidone (optionally cross-linked), also known as poly-N-vinyl-poly-2-pyrrolidone, and commonly abbreviated to "PVP" (optionally cross-linked PVP). PVP generally refers to a polymer containing vinylpyrrolidone (also referred to as N-vinylpyrrolidone, N-vinyl-2-pyrrolidone and N-vinyl-2-pyrrolidinone) as a monomeric unit. The monomeric unit may include a polar imide group, four non-polar methylene groups, and a non-polar methane group. Cross-linked PVP includes those commercially available as KOLLIDON® and LUVICROSS®, marketed by BASF, Mount Olive, N.J., USA; and POLYPLASDO E® INF-10, marketed by, Ashland, Covington, Kentucky, USA.

The compositions of the present disclosure can optionally contain whitening (oxidizing) agents in addition to the potassium peroxymonosulfate, but preferably no other whitening agents are included. Whitening agents are generally materials which are effective to provide whitening of a tooth surface to which it is applied via oxidative action, and include agents such as hydrogen peroxide and urea peroxide. In various embodiments, the compositions of the present disclosure may optionally comprise a peroxide whitening agent, comprising a peroxide compound, but preferably no peroxide whitening agents or no peroxide compounds are included. A peroxide compound is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof. In some embodiments, the peroxide compound comprises hydrogen peroxide. In some embodiments, the peroxide compound consists essentially of hydrogen peroxide. In some embodiments, the compositions may comprise a non-peroxide whitening agent. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. One or more additional whitening agents are optionally present in a tooth-whitening effective total amount. In some embodiments the compositions additionally comprise an activator, e.g., tetraacetylethylenediamine. In some embodiments, the compositions of the present invention are free of all of the above enumerated additional whitening agents.

In some embodiments, the compositions may comprise a non-oxidative whitening agent. Non-oxidative whitening agents include colorants, such as titanium dioxide and blue pigment or dye, and hydroxyapatite. These agents cause a whiter appearance of the teeth through masking or covering stains, but not chemically removing or destroying the stains.

The compositions of the present disclosure optionally can also include other ingredients, e.g., flavor agents; fillers; surfactants; preservatives, e.g., sodium benzoate and potassium sorbate; color agents including, e.g., dyes and pigments; and sweeteners. In some embodiments, the compositions of the present disclosure comprise one or more surfactants, such as anionic, cationic, zwitterionic or nonionic surfactants.

As used herein, "anionic surfactant" means those surface-active or detergent compounds that contain an organic hydrophobic group containing generally 8 to 26 carbon atoms or generally 10 to 18 carbon atoms in their molecular structure and at least one water-solubilizing group selected from sulfonate, sulfate, and carboxylate so as to form a water-soluble detergent. Usually, the hydrophobic group will comprise a $C_8$-$C_{22}$ alkyl, or acyl group. Such surfactants are employed in the form of water-soluble salts and the salt-forming cation usually is selected from sodium, potassium, ammonium, magnesium and mono-, di- or tri-$C_2$-$C_3$ alkanolammonium, with the sodium, magnesium and ammonium cations again being the usual ones chosen. Some examples of suitable anionic surfactants include, but are not limited to, the sodium, potassium, ammonium, and ethanolammonium salts of linear $C_8$-$C_{18}$ alkyl ether sulfates, ether sulfates, and salts thereof. Suitable anionic ether sulfates have the formula $R(OC_2H_4)_nOSO_3M$ wherein n is 1 to 12, or 1 to 5, and R is an alkyl, alkylaryl, acyl, or alkenyl group having 8 to 18 carbon atoms, for example, an alkyl group of $C_{12}$-$C_{14}$ or $C_{12}$-$C_{16}$, and M is a solubilizing cation selected from sodium, potassium, ammonium, magnesium and mono-, di- and triethanol ammonium ions. Exemplary alkyl ether sulfates contain 12 to 15 carbon atoms in the alkyl groups thereof, e.g., sodium laureth (2 EO) sulfate. Some preferred exemplary anionic surfactants that may be used in the compositions of the present disclosure include sodium laurel ether sulfate (SLES), sodium lauryl sulfate, and ammonium lauryl sulfate. In certain embodiments, the anionic surfactant is present in an amount of 0.01 to 5.0%, 0.1 to 2.0%, 0.2 to 0.4%, or about 0.33%.

As used herein, "nonionic surfactant" generally refers to compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name PLURONIC®), polyoxyethylene, polyoxyethylene sorbitan esters (sold under trade name TWEENS®), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, alkyl polyglycosides (for example, fatty alcohol ethers of polyglycosides, such as fatty alcohol ethers of polyglucosides, e.g., decyl, lauryl, capryl, caprylyl, myristyl, stearyl and other ethers of glucose and polyglucoside polymers, including mixed ethers such as capryl/caprylyl ($C_{8-10}$) glucoside, coco ($C_{8-16}$) glucoside, and lauryl ($C_{12-16}$) glucoside), long chain tertiary amine oxides, long chain tertiary phosphine oxides, long chain dialkyl sulfoxides, and mixtures of such materials.

In some embodiments, the nonionic surfactant comprises amine oxides, fatty acid amides, ethoxylated fatty alcohols, block copolymers of polyethylene glycol and polypropylene glycol, glycerol alkyl esters, polyoxyethylene glycol octylphenol ethers, sorbitan alkyl esters, polyoxyethylene glycol sorbitan alkyl esters, and mixtures thereof. Examples of amine oxides include, but are not limited to, laurylamidopropyl dimethylamine oxide, myristylamidopropyl dimethylamine oxide, and mixtures thereof. Examples of fatty acid amides include, but are not limited to, cocomonoethanolamide, lauramide monoethanolamide, cocodiethanolamide, and mixtures thereof. In certain embodiments, the nonionic surfactant is a combination of an amine oxide and a fatty acid amide. In certain embodiments, the amine oxide is a mixture of laurylamidopropyl dimethylamine oxide and myristylamidopropyl dimethylamine oxide. In certain embodiments, the nonionic surfactant is a combination of lauryl/myristylamidopropyl dimethylamine oxide and cocomonoethanolamide. In certain embodiments, the nonionic surfactant is present in an amount of 0.01 to 5.0%, 0.1 to 2.0%, 0.1 to 0.6%, 0.2 to 0.4%, about 0.2%, or about 0.5%.

As used herein, the term "cationic surfactant" includes the cationic surfactants disclosed in WO 2007/011552A2, the contents of which are incorporated herein by reference in its entirety.

Examples of the surfactant that can be used are sodium lauryl sulfate, sorbitan fatty acid ester, polyoxyethylene (20) sorbitan monooleate (Polysorbate 80 or Tween 80), polyethylene glycol fatty acid ester, polyoxyethylene sorbitan fatty acid ester, polyoxyethylene alkyl ether, polyoxyethylene polyoxypropylene alkyl ether, polyoxyethylene polyoxypropylene block copolymer, polyoxyethylene alkyl phenyl ether, polyoxyethylene castor oil, polyoxyethylene hydrogenated castor oil, polyoxyethylene sorbitol fatty acid ester and polyoxyethylene glycerol fatty acid ester. In the present invention, each of them may be used solely or two or more thereof may be used jointly. Typical amounts of surfactant are about 0.1% to about 3%, in one embodiment about 0.1% to about 2%, in another embodiment about 0.1% to about 1%, by weight of the total composition.

Examples of the filler are crystalline cellulose, ethylcellulose, dextrin, various kinds of cyclodextrin (α-cyclodextrin, β-cyclodextrin and γ-cyclodextrin), sodium sulfate, as well as derivatives thereof and pullulan.

Useful flavor agents include natural and synthetic flavoring sources including, e.g., volatile oils, synthetic flavor oils, flavoring aromatics, oils, liquids, oleoresins and extracts derived from plants, leaves, flowers, fruits, stems and combinations thereof. Suitable flavor agents include, e.g., citric oils, e.g., lemon, orange, grape, lime and grapefruit, fruit essences including, e.g., apple, pear, peach, grape, strawberry, raspberry, cherry, plum, pineapple, apricot, and other fruit flavors. Other useful flavor agents include, e.g., aldehydes and esters (e.g., benzaldehyde (cherry, almond)), citral, i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), 2-dodedenal (citrus, mandarin) and mixtures thereof.

Suitable coloring agents include, e.g., food, drug and cosmetic (FD&C) colors including, e.g., dyes, lakes, and certain natural and derived colorants. Useful lakes include dyes absorbed on aluminum hydroxide and other suitable carriers.

Suitable sweetening agents include stevia, sugars such as sucrose, glucose, invert sugar, fructose, ribose, tagalose, sucralose, maltitol, erythritol, xylitol, and mixtures thereof, saccharin and its various salts (e.g., sodium and calcium salt of saccharin), cyclamic acid and its various salts, dipeptide sweeteners (e.g., aspartame), acesulfame potassium, dihydrochalcone, glycyrrhizin, and sugar alcohols including, e.g., sorbitol, sorbitol syrup, mannitol and xylitol, and combinations thereof.

It is understood that while general attributes of each of the above categories of materials may differ, there may be some common attributes and any given material may serve multiple purposes within two or more of such categories of materials. All of the ingredients in the compositions may have functions in addition to their primary function, and may contribute to the overall properties of the composition, including its stability, efficacy, consistency, mouthfeel, taste, odor and so forth. For example, a binder may also function as a disintegrating agent and vice versa.

In a second aspect, the present disclosure provides a method for whitening teeth comprising the steps of (a) applying Composition 1, or any of 1.1 et seq., to the teeth, and (b) maintaining contact of the composition with the teeth for a sufficient period of time (e.g., 0.1 to 60 minutes, or 0.1 to 30 minutes, or 0.1 to 10 minutes, or 0.1 to 5 minutes, or 0.1 to 2 minutes, or 0.1 to 1 minute) to effect whitening of the teeth contacted by the composition. In some embodiments, the composition may be applied using a toothbrush, and the composition maintained in contact with the teeth by using a brushing action. In some embodiments, the composition may be applied to the teeth using a dental tray, and the composition maintained in contact with the teeth by placement of the dental tray in the mouth until whitening is complete.

In other embodiments, the present disclosure provides for the use Composition 1, or any of 1.1 et seq., or any other embodiments thereof, for the whitening of the teeth.

EXAMPLES

Exemplary embodiments of the present disclosure will be illustrated by reference to the following examples, which are included to exemplify, but not to limit the scope of the present invention.

In the examples and elsewhere in the description of the invention, chemical symbols and terminology have their usual and customary meanings. Temperatures are in degrees Celsius unless otherwise indicated. The amounts of the components are in weight percent based on the standard described; if no other standard is described then the total weight of the composition is to be inferred. Various names of chemical components include those listed in the CTFA International Cosmetic Ingredient Dictionary (Cosmetics, Toiletry and Fragrance Association, Inc., 7$^{th}$ ed. 1997).

Example 1: Exemplary MPS-Based Whitening Dentifrice

Potassium peroxymonosulfate is combined with calcium pyrophosphate, and other excipients and mixed to provide a homogenous product.

The compositions may have a formula as follows:

| Ingredient | Weight % |
|---|---|
| Potassium peroxymonosulfate | 0.1-5% (e.g., 1%) |
| Calcium pyrophosphate | 20-30% (e.g., 25%) |
| PEG/PPG triblock copolymer (e.g., Pluronic L35) | 25-35% (e.g., 31%) |
| Polyvinylpyrrolidone | 1-15% (e.g., 5%) |
| PEG-PPG random copolymer (e.g., PEG/PPG-116/66) | 6-15% (e.g., 10%) |
| Polyethylene glycol (e.g., PEG 600) | 10-20% (e.g., 12.5%) |
| Polyphosphate (e.g., sodium pyrophosphates) | 2.5-5% (e.g., 4%) |
| Anionic Surfactant (e.g., sodium lauryl sulfate) | 1-5% (e.g., 2%) |
| Zwitterionic Surfactant (e.g., cocamidopropyl betaine) | 0.1-1% (e.g., 0.3%) |
| Fluoride source (e.g., sodium monofluorophosphate) | 0.1 to 2% (e.g., 0.75%) |
| Antioxidant (e.g., BHT) | 0.01 to 0.3% (e.g., 0.03%) |
| Thickener (e.g., fumed silica) | 2.5-5% (e.g., 4%) |
| Sweeteners and Flavors | 0.5-5% |
| Blue pigment or dye (e.g., Blue 15) | 0.001 to 0.1% (e.g., about 0.05%) |
| Total | ca. 100 |

Testing of the formulas within the scope of the disclosure demonstrates that they provide improved stability and retained active oxygen activity compared to comparative formulas not within the scope of the present disclosure.

Example 2: MPS Stability

To evaluate the effect of replacing calcium pyrophosphate abrasive with high cleaning silica abrasive, four compositions are prepared according to the following Table:

| Ingredient | Comp. A | Comp. B | Comp. C. | Comp. D |
|---|---|---|---|---|
| Potassium peroxymonosulfate* | 1.0% | 1.0% | 1.0% | 1.0% |
| Calcium pyrophosphate | 25% | 15% | — | — |
| Synthetic high cleaning silica | — | — | 25% | 50% |
| PEG/PPG triblock copolymer | 31% | 36% | 32% | 25% |
| Polyvinylpyrrolidone | 5% | 23% | 4% | 1% |
| PEG-PPG random copolymer | 10% | 5% | 10% | 5% |
| Polyethylene glycol (e.g., PEG 600) | 12.5% | 10% | 12.5% | 7.5% |
| Tetrasodium pyrophosphate | 3% | 2% | 3% | 1.5% |
| Disodium pyrophosphate | 1% | 0.9% | 1% | 0.5% |
| Sodium lauryl sulfate | 2% | 2% | 2% | 2% |
| Cocamidopropyl betaine | 0.3% | — | 0.3% | 0.3% |
| Sodium monofluorophosphate | 0.76% | 0.76% | 0.76% | 0.76% |
| Antioxidant | 0.03% | — | — | — |
| Thickener | 4% | 2.3% | 4% | 1% |
| Sweeteners and Flavors | 3.35% | 0.54% | 3.25% | 3.25% |
| Total | ca. 100 | ca. 100 | ca. 100 | ca. 100 |

*provided as 2.2 wt. % Caroat (45 wt. % potassium monoperoxysulfate)

The Compositions A, B, C, and D, are compared in an accelerated aging study. Samples are placed in tubes and stored at 60° C./75% RH (relative humidity) for 2 weeks. Active oxygen (AO) levels are determined initially, and at 1 week and 2 weeks, by iodometric titration. The results are shown in the table below (expressed as percent of initial theoretical AO):

| Formula | Initial AO | AO at 1 week | AO at 2 weeks |
|---|---|---|---|
| Composition A | 100% | 94% | 94% |
| Composition B | 100% | 95% | 92.3% |
| Composition C | 95% | 53% | 41% |
| Composition D | 110% | 44% | 26% |

The results demonstrate that Compositions A and B, which are stabilized by calcium pyrophosphate abrasive and PEG/PPG triblock copolymer, retain nearly full active oxygen through the 2 week study. In contrast, using high cleaning silica abrasive (Compositions F, G), there is a rapid loss in active oxygen, due to decomposition of the potassium monoperoxysulfate. Without being bound by theory, it is believed that trace heavy metals in precipitated silica (such as high-cleaning silica) promotes catalytic decomposition of MPS (unlike fumed silica, which lacks such impurities). It is also noted that high cleaning silicas are more effective abrasives than calcium pyrophosphate (e.g., the RDA (relative dentin abrasivity) of high cleaning silica is about 160, but for calcium pyrophosphate it is about 90). Thus, this loss in abrasivity is a consequence of improving MPS stability.

Example 3: Rheology

Compositions A and B are compared using a Brookfield programmable viscometer during an aging study. All tests are performed with toothpastes in solid containers, 120 ml sample cups. The samples are stored for 2 or 3 months at 40° C./65% RH (relative humidity). A fresh spot is selected at least 1 cm from the wall of the jar and from spots of previous tests. The viscometer spindle is slowly lowered into the sample jar with as little disturbance of the sample as possible. Then the vane v74 spindle on the shaft of the viscometer is slowly lowered into the sample. A thixotropy loop test is performed according to the programmed software. Squeeze pressure (bar) is a measured to estimate the ability of a toothpaste or gel to be squeezed out of a tube. Acceptable squeeze pressures range from 0.03 to 0.1 bar, with about 0.05 bar being ideal. If the squeeze pressure is too low, the toothpaste will ooze out of the tube or be expelled from the tube too violently with gentle pressure. If the squeeze pressure is too high, the toothpaste will be too difficult to squeeze from the tube. Viscosity is measured at 1 rpm (in centipoise, cP). Viscosity for a toothpaste is preferably maintained during aging at 70,000 to 300,000 cP, most preferably at about 200,000 cP.

The results are shown in the table below (N.M.=not measurable, because the toothpaste could not be squeezed from the tube):

| Squeeze Pressure | Initial | 1 month | 2 months | 3 months |
|---|---|---|---|---|
| Composition A | 0.048 | 0.052 | 0.052 | 0.057 |
| Composition B | 0.080 | N.M. (>0.2 bar) | N.M. (>0.2 bar) | N.M. (>0.2 bar) |

| Viscosity (1 rpm) | Initial | 1 month | 2 months | 3 months |
|---|---|---|---|---|
| Composition A | 205,883 | 258,726 | 282,788 | 298,990 |
| Composition B | 368,676 | N.M. | N.M. | N.M. |

The results demonstrate that the compositions of the present invention retain stable rheological characteristics compared to similar compositions outside the scope of the present disclosure.

Example 4: Whitening Efficacy

Composition A is tested against Composition E for whitening efficiency. Composition E is a commercial whitening toothpaste composition with high-cleaning silica. Composition E comprises (in descending order of concentration): Glycerin, hydrated silica, sodium hexametaphosphate, aqua, PEG-6, aroma, silica, sodium lauryl sulfate, cocamidopropyl betaine, trisodium phosphate, mica, chondrus crispus powder, PEG-20M, sodium fluoride, xanthan gum, and sodium chloride, plus minor flavors, colors, and preservatives.

The heads of soft toothbrushes are cut from the handles and mounted for use on a brushing machine. Bovine teeth are mounted and stained with coffee and tea. Each toothpaste slurry is poured over each tray and brushing is immediately started on the teeth. The teeth are brushed for 2 minutes with 250 grams of pressure applied. The brushing machine is set to 120 strokes per minute. After 2 minutes, the brushing is stopped, the slurry is removed, and the teeth are rinsed with deionized water then dried. The brushing treatment is repeated a total of 14 times to model twice daily use of each product for 7 days.

Software from Medical High Technology (MHT) is used to measure the $L^*$, $a^*$, and $b^*$ values for each tooth before and after treatment. The $L^*$, $a^*$, and $b^*$ values are used to calculate the change in the whiteness index for each tooth after 14 treatments as compared to baseline. The Whiteness index is reported as $\Delta W^*$, wherein:

$$W^* = (a^{*2} + b^{*2} + (L^* - 100)^2)^{1/2}$$

$$\Delta W^* = W^*_{treated} - W^*_{baseline}$$

The absolute value of $\Delta W^*$ is reported. It should be noted that the more positive the value of $\Delta W^*$, the closer the tooth color is to white.

The Analysis of Variance test is used to compare the mean $\Delta W^*$ values for each product after 14 treatments. A subsequent Tukey multiple comparison test is performed in order to assess pair-wise comparisons of the products. A p-value less than 0.05 indicates statistically significant differences among the products.

The results are shown in the following table:

| | mean ΔW | |
|---|---|---|
| Treatment No. | Comp. A | Comp. E |
| 0 (initial) | 0.00 | 0.00 |
| 2 | 3.74 | 0.61 |
| 4 | 5.09 | 1.18 |
| 6 | 6.10 | 1.51 |
| 8 | 6.16 | 2.22 |
| 10 | 7.03 | 2.28 |
| 12 | 7.28 | 2.71 |
| 14 | 7.21 | 3.46 |

At treatment 14, the whitening results for Composition A are a statistically significant improvement over the whitening results for Composition E (p-value 0.0023). The results demonstrate that a whitening composition according to the present disclosure is highly effective, significantly more so than a current commercial whitening composition.

Example 5: Enhanced Whitening Efficacy with Blue Pigment

Teeth whitening is commonly performed using either abrasives (such as high-cleaning silica) to remove stain molecules from the surface of teeth, or using oxidizing agents to bleach out the color of stain molecules on the teeth, or both. The inventors have further discovered that using a blue pigment can mask the presence of stains by making the teeth appear whiter. This is important as both abrasive and oxidizing agents take some time (typically 1-2 weeks) to begin to show a substantial whitening effect, whereas the masking effect of blue pigment is much more immediate.

There compositions are compared in a whitening study. Composition A from Example 1, Composition A with 0.05% Blue 15 pigment (CI 74160) added, and a commercial whitening composition (Composition F) comprising 0.1% hydrogen peroxide and 0.05% Blue 15 pigment.

Extracted whole human molars are obtained from Therametric Technologies, Inc. The crowns and roots are separated and the isolated crowns are bisected longitudinally using a Buehler IsoMet low speed saw. The bisected crown pieces are mounted in a methacrylate resin so that only the enamel is exposed. 27 teeth are selected and three teeth are mounted per tray using a thermal setting impression compound. All nine trays are used to evaluate each product in a randomized order.

All measurements are taken with a Spectroshade Micro instrument manufactured by Medical High Technology (MHT). Before measuring the baseline optical properties of the teeth, the instrument is calibrated per the manufacturer's instructions. To take a measurement, the instrument is positioned so that one tooth is in the instrument's field of vision and then the image is captured. This is repeated for each measurement in the study.

A 1:2 (w/w) slurry of toothpaste to artificial saliva is prepared for each sample (e.g., about 250 g of toothpaste and 500 g of artificial saliva). The slurry is mixed by hand to completely homogenize the solution before addition to the tray.

The heads of soft toothbrushes are cut from the handles and mounted for use on a brushing machine. 9 mL of a standard toothpaste slurry is poured over each tray and brushing is immediately started. The teeth are brushed for 10 minutes with 250 grams of pressure applied. The brushing machine is set to 120 strokes per minute. After 10 minutes, the brushing is stopped, the slurry is removed, and the teeth are rinsed with deionized water then dried. Baseline spectrophotometer measurements are then taken. The teeth are then submerged in artificial saliva (9 mL/tray), and aged at 37° C. with agitation for 15 minutes. Then, the test toothpaste slurry is added to the tray, and the teeth are brushed for 2 minutes with 250 grams of pressure applied. The brushing machine is set to 120 strokes per minute. After 2 minutes, the brushing is stopped, the slurry is removed, and the teeth are rinsed with deionized water then dried. After-treatment spectrophotometer measurements are then taken. Data analysis is as described in Example 4.

The results are shown in the following table.

|  | mean ΔW |
| --- | --- |
| Composition A (1% MPS) | 7.20 |
| Composition A (1% MPS) + Blue 15 | 15.83 |
| Composition F (0.1% HP) + Blue 15 | 12.01 |

The results demonstrate that adding Blue 15 pigment enhances the immediate whitening effect (1 brushing cycle) of an MPS toothpaste according to the present disclosure. Furthermore, the whitening effect of the MPS combined with Blue 15 is greater than the same amount of Blue 15 added to a comparable hydrogen peroxide-based toothpaste composition (0.1% HP has an active oxygen content equivalent to 1% MPS).

The invention has been described above with reference to illustrative Examples, but it is to be understood that the invention is not limited to the disclosed embodiments. Alterations and modifications that would occur to one of skill in the art upon reading the specification are also within the scope of the invention, which is defined in the appended claims.

What is claimed is:

1. A tooth whitening oral care composition comprising 1% to 5% potassium peroxymonosulfate by weight, stabilized with a combination of 22% to 30% calcium pyrophosphate ($Ca_2P_2O_7$), by weight of the composition, and 25-35% polyoxyethylene/polyoxypropylene triblock copolymer having the formula $HO$—$[CH_2CH_2O]_a$—$[CH(CH_3)CH_2O$—$]_b$
    $[CH_2CH_2O]_a$—$H$, wherein a is an integer between 10 and 12, b is an integer between 15 and 20, by weight of the composition; and further comprising:
   6-15% of a PEG/PPG random copolymer, by weight of the composition;
   10 to 15% of a polyethylene glycol, by weight of the composition; and
   polyvinylpyrrolidone in an amount of 1 to 15%, by weight of the composition;
   wherein the composition is a toothpaste or tooth gel, and wherein the composition does not comprise hydrogen peroxide.

2. The composition of claim 1, wherein the potassium peroxymonosulfate is the only oxidizing agent present in the composition.

3. The composition of claim 1, wherein the composition is stabilized by 23% to 27% calcium pyrophosphate ($Ca_2P_2O_7$), by weight of the composition.

4. The composition of claim 3, wherein the composition comprises the calcium pyrophosphate in an amount of 24% to 26%, or about 25%, by weight of the composition.

5. The composition of claim 1, wherein the composition further comprises one or more of alkali metal polyphosphates, and anionic and/or zwitterionic surfactants.

6. The composition of claim 1, wherein the composition comprises a mixture of anionic and zwitterionic surfactants.

7. The composition of claim 6, wherein the composition comprises a mixture of sodium lauryl sulfate and cocamidopropyl betaine.

8. The composition of claim 7, wherein the composition comprises 2 to 4%, or 1 to 3%, or 2 to 3%, or 1.5 to 2.5%, or 2 to 2.5%, or about 2%, of sodium lauryl sulfate, and 0.1 to 1%, or 0.1 to 0.5%, or about 0.3%, of cocamidopropyl betaine, by weight of the composition.

9. The composition of claim 1, wherein the composition further comprises an antioxidant selected from butylated hydroxyanisole, butylated hydroxytoluene, vitamin A, carotenoids, vitamin E, flavonoids, polyphenols, ascorbic acid, and mixtures thereof.

10. The composition of claim 1, wherein the polyethylene glycol is selected from the group consisting of PEG-200, PEG-300, PEG-400, PEG-500, PEG-600, PEG-800, PEG-1000, PEG-1600, and PEG-2000.

11. The composition of claim 1, wherein the composition comprises the potassium peroxymonosulfate in an amount of 1% to 3%, by weight of the composition.

12. The composition of claim 1, wherein the PEG/PPG random copolymer has an average molar ratio of ethylene glycol units (EG) to propylene glycol units (PG) of about 105-125 EG to 55-75 PG and wherein the polyethylene glycol is polyethylene glycol 600 in an amount of 10 to 15%, each by weight of the composition.

13. The composition of claim 1, wherein the composition further comprises 2% to 5% tetrasodium pyrophosphate and 0.5 to 1.5% disodium pyrophosphate, by weight of the composition.

14. The composition of claim 1, wherein the composition further comprises a blue dye or pigment, optionally in an amount of 0.001 to 0.1% by weight of the composition.

15. A composition according to claim 1, wherein the composition comprises:

| Ingredient | Weight % |
| --- | --- |
| Potassium peroxymonosulfate | 1% |
| Calcium pyrophosphate | 25% |
| PEG/PPG triblock copolymer | 30-32% |
| Polyvinylpyrrolidone | 5% |
| PEG-PPG random copolymer | 10% |
| Polyethylene glycol | 12.5% |
| sodium pyrophosphates | 2.5-5% |
| sodium lauryl sulfate | 1-5% |
| cocamidopropyl betaine | 0.1-1% |
| sodium monofluorophosphate | 0.1 to 2% |
| Antioxidant | 0 to 0.3% |
| fumed silica | 2.5-5% |
| Sweeteners and Flavors | 0.5-5% |
| Blue pigment or dye | 0.001 to 0.1% |
| Total | ca. 100. |

16. A method for whitening teeth comprising the steps of (a) applying a composition according to claim 1, to the teeth, and (b) maintaining contact of the composition with the teeth for a sufficient period of time to effect whitening of the teeth contacted by the composition.

17. The composition according to claim 15, wherein the PEG/PPG triblock copolymer has the formula HO—[CH$_2$CH$_2$O]$_a$[—CH(CH$_3$)CH$_2$O—]$_b$[CH$_2$CH$_2$O]$_a$—H, wherein a is an integer between 10 and 12, and b is an integer between 15 and 20, wherein the PEG-PPG random copolymer is PEG/PPG 116/66, the polyethylene glycol is PEG-600, and the sodium pyrophosphates are tetrasodium and/or disodium pyrophosphates.

18. The composition of claim 1, wherein the composition has a viscosity (measured at 1 rpm) of 150,000 to 250,000 cP, or 175,000 to 225,000 cP, or about 200,000 cP, and/or wherein the composition has a squeeze pressure of 0.03 to 0.07 bar, or 0.04 to 0.06 bar, or about 0.05 bar.

19. The composition of claim 1, wherein after up to 3 months of aging at 40° C./65% relative humidity, the composition retains a squeeze pressure below 0.1 bar and/or a viscosity (at 1 rpm) below 300,000 cP.

20. The composition of claim 1, wherein the composition loses not more than 10% of its initial active oxygen (AO) content after up to 3 months of aging at 60° C./75% relative humidity.

* * * * *